(12) United States Patent
Yu et al.

(10) Patent No.: US 10,598,609 B2
(45) Date of Patent: Mar. 24, 2020

(54) UNIVERSAL LIQUID SAMPLE DEVICE AND PROCESS FOR HIGH RESOLUTION TRANSMISSION ELECTRON MICROSCOPE IMAGING AND MULTIMODAL ANALYSES OF LIQUID SAMPLE MATERIALS

(71) Applicant: BATTELLE MEMORIAL INSTITUTE, Richland, WA (US)

(72) Inventors: Xiao-Ying Yu, Richland, WA (US); Libor Kovarik, West Richland, WA (US); Bruce W. Arey, Kennewick, WA (US)

(73) Assignee: Battelle Memorial Institute, Richland, WA (US)

( * ) Notice: Subject to any disclaimer, the term of this patent is extended or adjusted under 35 U.S.C. 154(b) by 46 days.

(21) Appl. No.: 15/483,939

(22) Filed: Apr. 10, 2017

(65) Prior Publication Data

US 2017/0213692 A1 Jul. 27, 2017

Related U.S. Application Data

(63) Continuation-in-part of application No. 15/056,880, filed on Feb. 29, 2016, which is a continuation of
(Continued)

(51) Int. Cl.
*G01N 23/02* (2006.01)
*H01J 37/16* (2006.01)
(Continued)

(52) U.S. Cl.
CPC ......... *G01N 23/02* (2013.01); *G01N 23/2204* (2013.01); *H01J 37/16* (2013.01);
(Continued)

(58) Field of Classification Search
CPC .... G01N 23/00; G01N 23/22; G01N 23/2204; G01N 23/08; G01N 23/083; G01N 23/09;
(Continued)

(56) References Cited

U.S. PATENT DOCUMENTS

| 4,860,224 A | 8/1989 | Cashell et al. |
| 6,758,961 B1 | 7/2004 | Vogel et al. |

(Continued)

FOREIGN PATENT DOCUMENTS

| CN | 1053907162 | 3/2016 |
| EP | 2075821 A2 | 1/2009 |

(Continued)

OTHER PUBLICATIONS

Bard, A. J., et al., Introductory Lecture Studies of the Liquid/Solid Interface by Scanning Tunnelling Microscopy and Scanning Electrochemical Microscopy, Faraday Discuss, 94, 1992, 1-22.
(Continued)

*Primary Examiner* — Nathaniel J Kolb
(74) *Attorney, Agent, or Firm* — Wells St. John P.S.

(57) ABSTRACT

Liquid sample imaging devices and processes are disclosed for high resolution TEM imaging and multimodal analyses of liquid sample materials in situ under high vacuum that are compatible with standard type TEM chip membranes and TEM sample holders allowing TEM liquid sample imaging to be performed wherever a TEM instrument is accessible and at a substantially reduced cost compared to prior art systems and approaches.

17 Claims, 8 Drawing Sheets

Related U.S. Application Data application No. 14/050,144, filed on Oct. 9, 2013, now Pat. No. 9,274,059, which is a continuation-in-part of application No. 13/047,025, filed on Mar. 14, 2011, now Pat. No. 8,555,710.

(51) Int. Cl.
   H01J 37/26 (2006.01)
   H01J 37/20 (2006.01)
   G01N 23/2204 (2018.01)

(52) U.S. Cl.
   CPC .............. *H01J 37/20* (2013.01); *H01J 37/26* (2013.01); *H01J 2237/2802* (2013.01)

(58) Field of Classification Search
   CPC ......... G01N 23/12; G01N 2035/00148; G01N 2035/00158; B01L 2300/0816; B01L 3/5027; C12Q 2565/629; C12M 23/16; H01J 2237/2802; H01J 2237/2007; H01J 37/16; H01J 37/261
   USPC ....... 73/64.41, 64.55, 64.56, 865.6; 250/428, 250/430, 435, 438; 850/9, 12, 14, 15
   See application file for complete search history.

(56) References Cited

U.S. PATENT DOCUMENTS

| | | | |
|---|---|---|---|
| 7,201,836 B2 | 4/2007 | Vogel et al. | |
| 7,204,139 B2 | 4/2007 | Takayama | |
| 7,244,349 B2 | 7/2007 | Vogel et al. | |
| 7,387,715 B2 | 8/2008 | Vogel et al. | |
| 7,906,760 B2 | 3/2011 | Nishiyama et al. | |
| 8,059,271 B2 | 11/2011 | Marsh et al. | |
| 8,102,523 B1 | 1/2012 | Marsh et al. | |
| 8,555,710 B2 | 10/2013 | Yu et al. | |
| 9,022,662 B2 | 5/2015 | Chupas et al. | |
| 9,274,059 B2 | 3/2016 | Yu et al. | |
| 9,324,539 B2 | 4/2016 | Damiano, Jr. et al. | |
| 9,594,034 B1 | 3/2017 | Pompa | |
| 2004/0046120 A1* | 3/2004 | Moses .................... | H01J 37/20 250/311 |
| 2005/0045821 A1 | 3/2005 | Noji et al. | |
| 2005/0233066 A1 | 10/2005 | Sunagawa et al. | |
| 2006/0199260 A1 | 9/2006 | Zhang et al. | |
| 2007/0145287 A1 | 6/2007 | Chao et al. | |
| 2007/0231850 A1 | 10/2007 | Geoffrey et al. | |
| 2007/0267295 A1 | 11/2007 | Chang | |
| 2008/0057570 A1* | 3/2008 | Natarajan .............. | A61B 5/685 435/287.1 |
| 2009/0166536 A1 | 7/2009 | Suga et al. | |
| 2009/0294702 A1 | 12/2009 | Imanishi et al. | |
| 2009/0323069 A1 | 12/2009 | Naessens et al. | |
| 2010/0193398 A1 | 8/2010 | Marsh et al. | |
| 2012/0017415 A1 | 1/2012 | Marsh et al. | |
| 2012/0148880 A1 | 6/2012 | Schaefer et al. | |
| 2012/0234082 A1 | 9/2012 | Yu et al. | |
| 2012/0298883 A1* | 11/2012 | Grogan .................. | H01J 37/20 250/440.11 |
| 2014/0093052 A1 | 4/2014 | Chupas et al. | |
| 2016/0071685 A1* | 3/2016 | Kawanishi .............. | H01J 37/18 250/396 R |

FOREIGN PATENT DOCUMENTS

| | | |
|---|---|---|
| EP | 2388575 A1 | 11/2011 |
| JP | 2002148157 A | 5/2002 |
| KR | 100956165 B1 | 5/2010 |
| WO | 2011009209 A1 | 1/2011 |
| WO | 2012125216 A1 | 9/2012 |
| WO | WO 2016/068710 | 5/2016 |
| WO | WO PCT/US2018/026708 | 10/2019 |

OTHER PUBLICATIONS

Forest, M. L., et al., In situ X-ray analysis under controlled potential conditions: An innovative setup and its application to the investigation of ultrathin films electrodeposited on Ag(1 1 1), Electrochimica Acta, 51, 2006, 5532-5539.

Gao, X., et al., Sensitivity of Electrochemical Adlayer Structure to the Metal Crystallographic Orientation: Potential-Dependent Iodide Adsorption on Au(100) in Comparison with Other Low-Index Surfaces, J Phys Chem, 98, 1994, 8086-8095.

Hamelin, A., Cyclic voltammetry at gold single-crystal surfaces. Part 1. Behaviour at low-index faces, Journal of Electroanalytical Chemistry, 407, 1996, 1-11.

Hamelin, A., et al., Cyclic voltammetry at gold single-crystal surfaces. Part 2. Behaviour of high-index faces, Journal of Electroanalytical Chemistry, 407, 1996 13-21.

Hirschberg, D., et al., Identification of Endothelial Proteins by MALDI-MS Using a Compact Disc Microfluidic System, The Protein Journal, 23, 4, 2004, 263-271.

Hua, X., et al., In situ molecular imaging of a hydrated biofilm in a microfluidic reactor by ToF-SIMS, Analyst, 139, 2014, 1609-1613.

Itaya, K., In Situ Scanning Tunneling Microscopy in Electrolyte Solutions, Progress in Surface Science, 58, 3, 1998, 121-248.

Lee, J., et al., Development of an Automated Digestion and Droplet Deposition Microfluidic Chip for MALDI-TOF MS, American Society for Mass Spectrometry, 2008, doi:10.1016/j.jams.2008.03-15.

Liu, J., et al., Electrophoresis Separation in Open Microchannels. A Method for Coupling Electrophoresis with MALDI-MS, Anal Chem, 73, 2001, 2147-2151.

Liu, B., et al., In situ chemical probing of the electrode-electrolyte interface by ToF-SIMS, Lab on a Chip, 14, 2014, 855-859.

McDonald, J. C., et al., Poly(dimethylsiloxane) as a Material for Fabricating Microfluidic Devices, Accounts of Chemical Research, 35, 7, 491-499.

Murray, K. K., et al., Liquid Sample Introduction for Matrix-Assisted Laser Desorption Ionization, Anal Chem, 65, 1993, 2534-2537.

Ocko, B. M., et al., Structure and Electrocompression of Electrodeposited Iodine Monolayers on Au(111), J Phys Chem, 98, 1994, 897-906.

Onnerfjord, P., et al., Homogeneous Sample Preparation for Automated High Throughput Analysis with Matrix-assisted Laser Desorption/Ionisation Time-of-flight Mass Spectrometry, Rapid Communications in Mass Spectrometry, 13, 1999, 315-322.

Orsnes, H., et al., A Rotating Ball Inlet for On-Line MALDI Mass Spectrometry, Anal Chem, 72, 2000, 251-254.

Preisler, J., et al., On-Line MALDI-TOF MS Using a Continuous Vacuum Deposition Interface, Analytical Chemistry, 70, 24, 1998, 5278-5287.

Scherb, G., et al., In situ x-ray standing-wave analysis of electrodeposited Cu monolayers on GaAs(001), Physical Review B, 16, 1998, 800-805.

Sherwood, P. M. A., et al., Probing electrode surface chemical composition with core and valence band photoemission and an anaerobic cell, Colloids and Surfaces A: Physicochemical and Engineering Aspects, 134, 1998, 221-230.

Somorjai, G. A., Molecular level studies of solid-gas and solid-liquid interfaces, Surface Science, 335, 1995, 10-22.

Somorjai, G. A., et al., Concepts, instruments, and model systems that enabled the rapid evolution of surface science, Surface Science, 603, 2009, 1293-1300.

Somorjai, G. A., et al., Impact of Surface Chemistry, PNAS, 108, 3, 2011, 917-924.

Stuve, E. M., et al., Chemistry and physics of the "liquid"/solid interface: A surface science perspective, J Vac Sci Technol A, 11, 4, 1993, 2217-2224.

Tao, N. J., et al., In Situ Scanning Tunneling Microscopy Study of Iodine and Bromine Adsorption on Au(111) under Potential Control, J Phys Chem, 96, 1992, 5213-5217.

(56) References Cited

OTHER PUBLICATIONS

Wang, J., et al., In situ x-ray-diffraction and -reflectivity studies of the Au(111)/electrolyte interface: Reconstruction and anion adsorption, Physical Review B, 46, 16, 1992, 321-338.
Warren, S., et al, X-Ray Structural Analysis of Semiconductor-Electrolyte Interfaces, Physics at Surfaces and Interfaces, 2003, 22-38.
Wu, F., et al., Advances in sealed liquid cells for in-situ TEM electrochemical investigation of lithium-ion battery, Nano Energy, 11, 2015, 196-210.
Yamada, T., et al., Structure of Electrochemically Deposited Iodine Adlayer on Au(111) Studied by Ultrahigh-Vacuum Instrumentation and in Situ STM, J Phys Chem, 99, 1995, 8817-8823.
Yamada, T., et al., Interfacial structure of iodine electrodeposited on Au(111): studies by LEED and in situ STM, Surface Science, 335, 1995, 204-209.
Yang, L., et al., Probing liquid surfaces under vacuum using SEM and ToF-SIMS, Lab Chip, 11, 2011, 2481-2484.
Yang, L., et al., Making a hybrid microfluidic platform compatible for in situ imaging with vacuum-based techniques, J Vac Sci Technol A, 29, 6, 2011, 061101-1-061101-10.
Yang, L., et al., Performance of a microfluidic device for in situ ToF-SIMS analysis of selected organic molecules at aqueous surfaces, Analytical Methods, 5, 2013, 2515-2522.
Yang, , L., et al., In situ SEM and ToF-SIMS analysis of IGG conjugated gold nanoparticles at aqueous surfaces, Surl Interface Anal, 46, 2014, 224-228.
Yu, , X-Y., et al., Probing Aqueous Surfaces by TOF-SIMS, Current Trends in Mass Spectrometry, 2011, 34-39.
Yu, X-Y., et al., Imaging liquids using microfluidic cells, Microfluid Nanofluid, 15, 2013, 725-744.
Zhang, X., et al., On-Line Single Droplet Deposition for MALDi Mass Spectrometry, American Society for Mass Spectrometry, J Am Soc Mass Spectrom, 15, 2004, 1471-1477.
WO PCT/US2012/020136 IPRP, dated Sep. 17, 2013, Battelle Memorial Institute.
WO PCT/US2012/020136 Search. Rept., dated Aug. 21, 2012, Battelle Memorial Institute.
WO PCT/US2012/020136 Writ. Opin., dated Aug. 21, 2012, Battelle Memorial Institute.
Balasubramanian, M., et al., In situ X-ray diffraction and X-ray absorption studies of high-rate lithium-ion batteries, Journal of Power Sources, 92, 2001, 1-8.
Batina, N., et al., Atomic Level Characterization of the Iodine-Modified Au(111) Electrode Surface in Perchioric Acid Solution by in-Situ STM and ex-Situ LEED, Langmuir, 11, 1995, 4568-4576.
Chen, A., et al., Iodide adsorption at the Au(111) electrode surface, Journal of Electroanalytical Chemistry, 467, 1999, 342-353.

Dowsett, M. G., et al., Cell for Simultaneous Synchotron Radiation X-ray and Electrochemical Corrosion Measurements on Cultural Heritage Metals and Other Materials, Anal. Chem., 78, 2006, 3360-3365.
Gu, N., et al., Simultaneous determination of both the calibration constant in an electrochemical quartz crystal microbalance and the active active surface area of polycrystalline gold electrode, Electrochemistry Communications, 2, 2000, 48-50.
Hightower, A., et al., A study of iodine adlayers on polycrystalline gold electrodes by in situ electrochemical Rutherford backscattering (ECRBS), Electrochimica Acta, 54, 2009, 1777-1783.
Lei, H-W., et al., Electrochemical Quartz Crystal Microbalance Study of Halide Adsorption and Concomitant Change of Surface Excess of Water on Highly Ordered Au(111), Langmuir, 13, 1997, 3523-3528.
Leriche, J. B., et al., An electrochemical Cell for Operando Study of Lithium Batteries Using Synchotron Radiation, Journal of the Electrochemical Society, 157, 5, 2010, A606-A610.
Ogaki, K., et al., In Situ Scanning Tunneling Microscopy of Underpotential and Bulk Deposition of Silver and Gold (111), Electrochimica Acta, 40, 10, 1995, 1249-1257.
Roberts, G. A., Reflection-mode x-ray powder diffraction cell for in situ studies of electrochemical reactions, Review of Scientific Instuments, 75, 5, 2004, 1251-1254.
Rodriguez, J. F., et al., Determination of the Surface Area of Gold Electrodes by Iodine Chemisorption, J. Electroanal. Chem., 233, 1987, 283-289.
Scherb, G., et al., A novel thick-layer electrochemical cell for in situ x-ray diffraction, Review of Scientific instruments, 69, 2, 1998, 512-516.
Stuve, E. M., et al., Relating the in-situ, ex-situ, and non-situ envoronments in surface electrochemistry, Surface Science, 335, 1995, 177-184.
Szakal, C., et al., Surface Sensitivity in Cluster-Ion-Induced Sputtering, Physical Review Letters, 96, 2005, 216104.
WO PCT/US2018/026708 Search Rept., dated Oct. 15, 2016, Battelle Memorial Institute.
WO PCT/US2018/026708 Writ. Opin., dated Oct. 5, 2018, Battelle Memorial Institute.
Itaya et al., "In Situ Scanning Tunneling Microscopy of Organic Molecules Adsorbed on Iodine-Modified Au(111), Ag(111), and Pt(111) Electrodes", Solid-Liquid Electrochemical Interfaces, American Chemical Society, 665, 1997, United States, pp. 171-188.
Holtz, Megan et al., Nanoscale Imaging of Lithium Ion Distribution in Situ Operation of Battery Electrode and Electrolyte, Cornell University arXiv, Nov. 2013, United States, 2013.
Wilson, James, et al., Measurement of three-dimensional Microstructure in a LiCoO2 positive electrode. Journal of Power Sources 196 (2011) 3443-3447, United States, 2011.

* cited by examiner

UNIVERSAL LIQUID SAMPLE DEVICE AND PROCESS FOR HIGH RESOLUTION TRANSMISSION ELECTRON MICROSCOPE IMAGING AND MULTIMODAL ANALYSES OF LIQUID SAMPLE MATERIALS

CROSS REFERENCE TO RELATED APPLICATIONS

This application is a Continuation-in-Part of U.S. patent application Ser. No. 15/056,880 filed Feb. 29, 2016, which is a Continuation of U.S. patent application Ser. No. 14/050,144 filed Oct. 9, 2013 now issued as U.S. Pat. No. 9,274,059, which is a Continuation-in-Part of U.S. patent application Ser. No. 13/047,025 filed Mar. 14, 2011 now issued as U.S. Pat. No. 8,555,710, the contents of which are incorporated in their entirety herein.

STATEMENT REGARDING RIGHTS TO INVENTION MADE UNDER FEDERALLY-SPONSORED RESEARCH AND DEVELOPMENT

This invention was made with Government support under Contract DE-AC05-76RL01830 awarded by the U.S. Department of Energy. The Government has certain rights in the invention.

FIELD OF THE INVENTION

This invention relates generally to transmission electron microscopy (TEM) and more particularly to TEM liquid sample imaging systems and processes.

BACKGROUND OF THE INVENTION

Surging interest in studying liquids using the Transmission Electron Microscope (TEM) platform has led to the development of specialized liquid sample holders for TEM imaging of liquids. However, these specialized liquid sample holders require specialized chips that have limited dimensions and are typically not compatible with standard TEM chips and standard TEM solid sample holders. In addition, many times these devices will also require custom sealing approaches typically involving O-ring seals that limit types of liquid samples that can be analyzed. These limitations typically will raise purchase prices up to 8 times greater than standard chips and sample holders. In addition, specialized liquid sample holders typically do not address a well-known problem of liquid sample bulging that occurs in liquid samples from gas build up in the sealed sample holders. This gas build up can distort these liquids and the holders during TEM imaging and as a result the field of view is typically poor, image resolution suffers and overall sample viewing is typically limited.

A recent innovation by the same research group has produced a System for Analysis of Surfaces of Liquids at the Liquid Vacuum Interface (SALVI) (described in issued U.S. Pat. No. 8,555,710 and progeny thereof cited above) that allow for imaging of liquid surfaces with advantages not seen in the prior art. These include vacuum compatibility and low cost fabrication which also allows multimodal analyses of the same sample by multiple analysis platforms. In addition to these advantages various additional modifications have enhanced the capability of the original design. The present description provides a sample holder device that enables TEM imaging to be transmitted through the sample. These TEM liquid sample holders are compatible with standard TEM chips and TEM sample holders and can eliminate the need for specialized liquid sample holders and chips. These sample holders enable multimodal analyses of the same liquid samples utilizing multiple instrument platforms, and have a lower fabrication cost. This improved system and device provide for better results with lower costs and are another advancement in the development of improved sample processing technologies.

SUMMARY

The present invention is a TEM liquid sample device for static and dynamic TEM imaging and multimodal analyses of liquid samples in situ. The device includes a sample chamber formed by a pair of membranes. Membranes can be made of various materials including silicon containing materials, ceramics, glass, graphene, including combinations of these materials. Each membrane includes a non-opaque window. At least one membrane includes a vent aperture. These devices allow the liquid sample to be held in the sample chamber without an O-ring type seal. The sample chamber holds a selected quantity of a liquid sample while a probe beam passes through the window and internal gases are vented through the vent aperture. Vent apertures may include various sizes and dimensions in order to retain the liquid sample within the sample chamber when the TEM vacuum is applied. In some embodiments and applications the liquid sample has a generally uniform thickness. In some embodiments these devices include a sample injection port or valve to allow delivery of the liquid sample to the sample chamber. In some embodiments a frame is sandwiched between the two membranes to impart a preselected height to the sample chamber. In some embodiments a spacer is positioned on one or both of the membranes between the membrane and the sample chamber to enhance optical characteristics of images created by the probe beam such as an enhanced image resolution or an enhanced field of view. Spacers of varying thicknesses may be utilized to enable formation of various liquid sample layer thicknesses in the sample chamber between the membranes for imaging and multimodal analyses. In some embodiments windows on one membrane are not identical to windows on the second membrane. In some embodiments the first membrane includes a different number of windows than the second membrane. At least one window in each membrane is aligned with the other to form a probe beam transmission zone through which the probe beam passes. In some applications windows are orthogonally aligned. In some applications vent apertures are positioned outside the probe beam transmission zone. In some embodiments the vent aperture is not a probe beam aperture. These assembled devices insert into standard type TEM solid sample holders and TEM solid sample heating holders and sample holders of other instrument platforms enabling multimodal imaging and analyses of liquid samples without modification of these standard type sample holders which is an advantage over TEM liquid sample holders known in the prior art.

In use embodiments of these TEM devices may be utilized for static and dynamic TEM imaging and multimodal analyses of liquid samples and materials therein. In one embodiment the method includes interrogating the liquid sample in the sample chamber formed by a pair of membranes. Each membrane includes a non-opaque window and at least one membrane forms a vent aperture. The sample chamber holds a preselected quantity of the liquid sample therein while a probe beam passes through the window and internal gases are vented through the vent aperture. Venting of the internal gases includes delivering the gases to the TEM vacuum when the TEM vacuum is applied. In some applications interrogating the liquid sample includes holding the liquid sample in a generally uniform thickness in the sample chamber while passing the probe beam through the windows and through the liquid sample of the sample chamber while venting the internal gases through the vent aperture. This arrangement allows imaging of the liquid sample to be performed at spatial resolutions as low as one nanometer or less.

The purpose of the foregoing abstract is to enable the United States Patent and Trademark Office and the public generally, especially the scientists, engineers, and practitioners in the art who are not familiar with patent or legal terms or phraseology, to determine the nature and essence of the technical disclosure of the application. The abstract is neither intended to define the invention of the application, which is measured by the claims, nor is it intended to be limiting as to the scope of the invention in any way.

DETAILED DESCRIPTION OF THE INVENTION

Figure 1A:
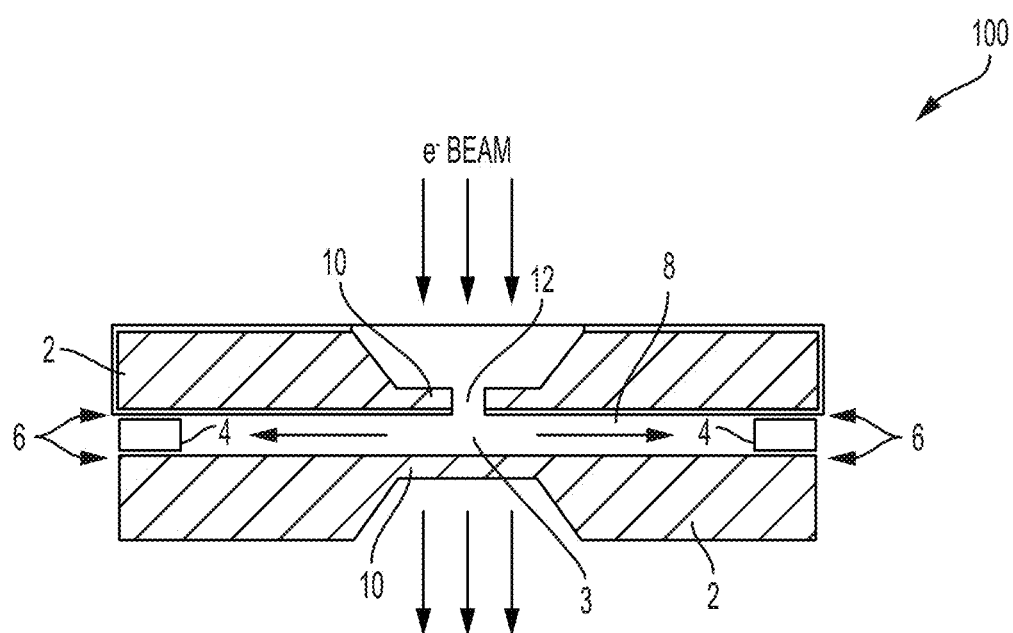
FIG. 1A-1C show different views of different embodiments of the present invention.

A TEM liquid sample device that enables TEM imaging and multimodal analyses of liquid samples and materials in situ and methods of using same are described. While various modes are shown for carrying out the invention it will be clear that the invention is susceptible to various modifications and alternative constructions. Accordingly, the description of the embodiments provided hereafter should be seen as illustrative only and not limiting.

FIGS. 1-4 show various features and embodiments of one disclosure of the invention. Referring now to FIG. 1A, one embodiment of a TEM liquid sample device 100 is shown. Device 100 includes a pair of membranes 2 that form a sample chamber 3 into which the liquid sample is introduced between the membranes. Membranes are made of a TEM vacuum compatible material such as ceramics including silicon nitride (SiN), silicon containing materials such as SiO2, other materials such as glass, graphene, and combinations of these various materials. Membranes 2 may include various shapes such as round and square and various thicknesses. In the figure, device 100 includes a support frame 4 sandwiched between the membranes made of an inert and vacuum compatible material such as silicon (Si). Support frame 4 may include various thicknesses. Membranes 2 may include an optional spacer 6 made of an inert material that attaches to and circumvolves the outer edge of a surface of the membranes. Spacers 6 may be attached using methods known in the chip fabrication arts such as spin coating. Spacer 6 thicknesses (Z-direction) determine the thickness or depth of the liquid sample layer 8 in the sample chamber 3 between the membranes 2 in the assembled device 100. Liquid layer thickness also depends in part on such factors as type of liquid; liquid physical properties such as viscosity; materials in the liquid being imaged or analyzed such as biological materials, crystalline materials, and particulate materials; material concentrations and volumes; and other like factors. Membranes include an electron transparent (non-opaque) window 10 made of a TEM vacuum compatible material such as a silicon nitride (SiN) ceramic, other silicon containing materials such as silicon dioxide (SiO2), and other suitable materials disclosed above. In preferred embodiments windows 10 are composed of a same material as the membranes 2 to minimize fabrication costs but window materials are not intended to be limited. Windows 10 may include various shapes, dimensions, and orientations in selected arrangements or chip patterns. And, various numbers of windows may also be utilized as described further in reference to FIG. 2 hereafter. Windows 10 are introduced into the membranes 2 using methods known in the chip fabrication arts such as wet etching, dry etching, and laser lithography. A vent aperture 12 is shown positioned in one membrane 2 that provides dynamic release of internal gases formed in the liquid sample 8 in the sample chamber 3 that maintains uniformity of the liquid sample layer 8 in the sample chamber 3 while liquid sample imaging is performed in the TEM under high vacuum, which enhances effective liquid sample viewing area in the TEM as well as resolution in images created while imaging these liquid samples. Vent aperture 12 is introduced into the chip membrane by methods such as laser drilling or combined Scanning Electron Microscope (SEM)/Focused Ion Beam (SEM-FIB) drilling. In the figure the gas release vent 12 is positioned in the membrane 2 of the assembled device above the liquid sample layer 8 in the sample chamber 3 but is not intended to be limited thereto. For example, in some embodiments one or more vent apertures are positioned in each membrane 2 above and below the liquid sample layer 8. Various arrangements may be utilized as detailed further in reference to FIG. 2. Vent apertures 12 of various sizes may also be utilized to accommodate TEM liquid sample devices with different and smaller dimensions; different spatial depths; different liquid types and liquid sample materials; different liquid sample properties such as viscosity; different sample liquid thicknesses, spatial resolutions, and spatial depths as well as process conditions such as sample heating or cooling during TEM and multimodal imaging. This capability to release internal gases from the liquid sample provides a unique and non-obvious innovation that addresses the well-known problem of sample bulging not provided by conventional TEM liquid sample devices and approaches that retain these gases in the sealed sample devices during TEM imaging known to generally reduce both the effective sample viewing area as well as the image resolution in these prior art devices.

Figure 1B:
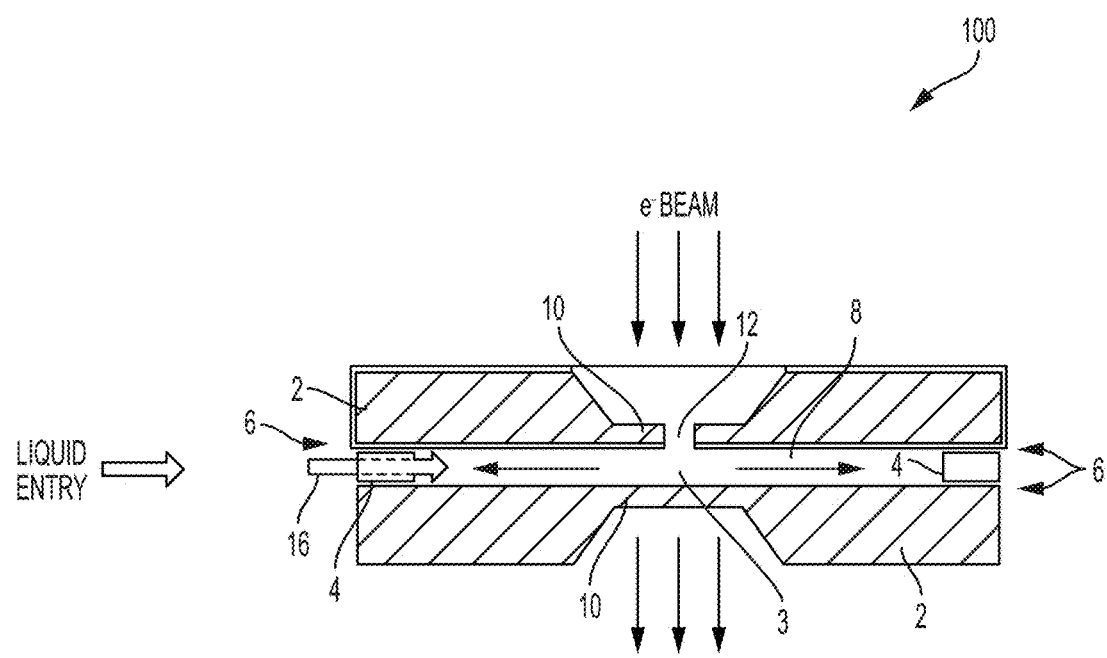

FIG. 1B shows another embodiment of the TEM liquid sample device 100. In addition to components described previously this embodiment also includes an injection port 16 or other introduction device 16 that delivers the liquid sample 8 into the sample chamber 3 between the membranes 2 of the assembled device. In the figure the injection port 16 is shown positioned so as to introduce liquid sample 8 into the sample chamber 3 through one end of the support frame 4 but positions are not intended to be limited.

Figure 1C:
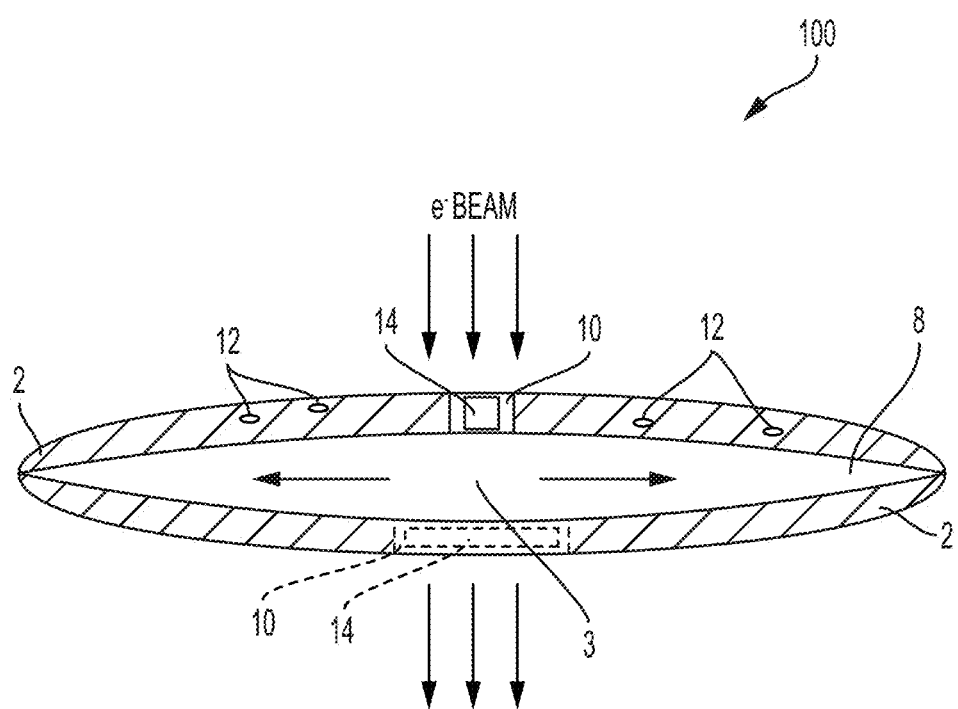

FIG. 1C shows yet another embodiment of the TEM liquid sample device 100. In this embodiment device 100 includes a sample chamber 3 sandwiched between a pair of membranes 2 that encloses the liquid sample 8 with transmission windows 10 in each of the membranes 2. This embodiment utilizes no frame or spacer as in embodiments described previously. Vent apertures 12 are shown positioned in one of the membranes 2 outside probe beam transmission zone 14, but number of vent apertures and their position in one or more membranes 2 are not intended to be limited.

Figure 2A:
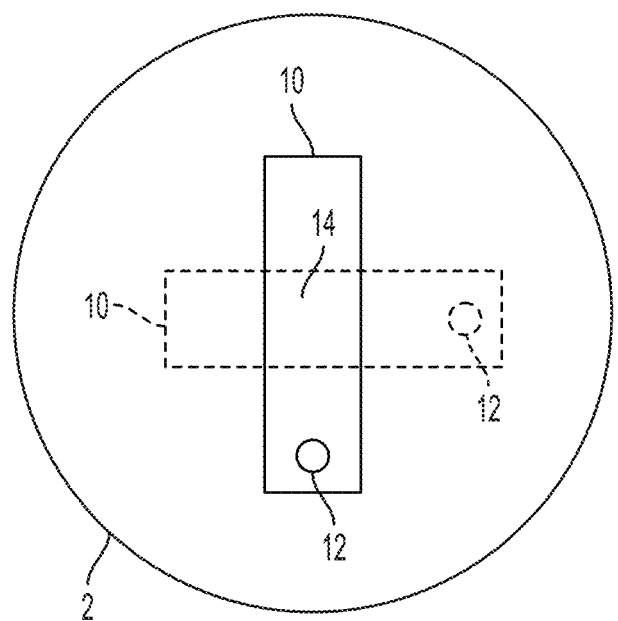
FIGS. 2A-2B show different window configurations utilized in accordance with the present invention.
Figure 2B:
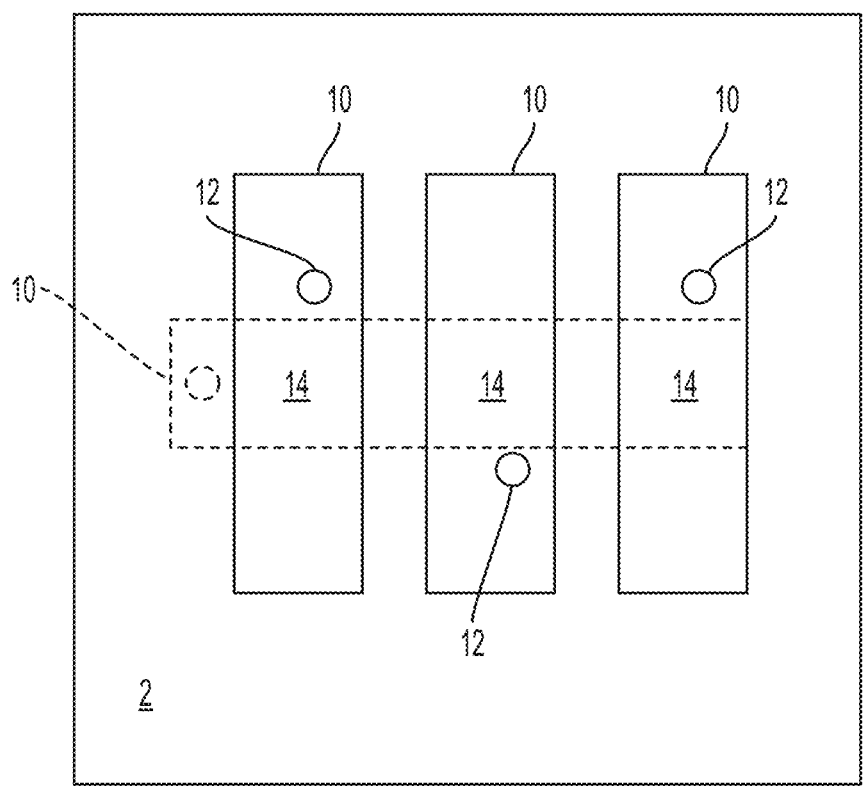

Assembled TEM liquid sample devices 100 of the present invention insert directly into standard type TEM solid sample holders and heating holders such as Gatan® TEM sample holders without modification of these sample holders enabling standard instrument equipment to be utilized at a substantially reduced cost that is another capability not provided by TEM liquid sample devices in the prior art. FIG. 2A is a top surface view showing one exemplary arrangement and alignment of single windows 10 in one embodiment of an assembled TEM liquid sample device 100 of the present invention in respective membranes 2. In this embodiment chip membranes 2 are round. Each window 10 also has a rectangular shape with an orientation that is orthogonal to the window 10 in the respective membrane 2. In this aligned position the windows 10 in each of the membranes 2 forms a transmission zone 14 through which the TEM electron probe beam is transmitted through the liquid sample positioned in the sample chamber between the respective membranes 2. A gas release vent 12 is also shown in each membrane 2 window 10 positioned so as to be above and below the liquid sample (not shown) but are not intended to be limited thereto. FIG. 2B shows another exemplary arrangement and alignment of windows 10 in another assembled TEM liquid sample device 100. In this embodiment chip membranes 2 are square. In this exemplary arrangement a top membrane 2 includes three windows 10 positioned adjacent to each other with a single window positioned in a bottom membrane 2 oriented orthogonal to windows in the top membrane 2 forming three transmission zones 14 in this particular alignment and arrangement. Gas release vents 12 are shown positioned at various locations in respective membrane 2 windows 10 but again are not intended to be limited thereto. In preferred embodiments gas release vents 12 are positioned in windows 10 outside the transmission zone 14 so as not to interfere with transmission of the electron probe beam through the membrane windows 10. Other window orientations and arrangements may also be utilized such as a parallel orientation or orientations between the orthogonal and parallel positions.

In use the TEM electron probe beam passes through the transmission zone 14 of the first membrane window 10 then proceeds through the liquid sample and exits the device through the transmission zone 14 of a second window 10 in the opposing membrane 2. Images of the liquid sample and materials therein formed by interaction of the electron probe beam with the liquid sample and materials therein in situ are collected by a TEM image collection plate or other detectors (not shown) from which images of the liquid samples and materials can be generated. Multimodal imaging and analyses of the same liquid sample materials in other analytical platforms can also be performed such as in electron diffraction (ED) and crystal diffraction instruments and platforms, Helium Ion Microscopes (HeIM), Scanning Electron Microscopes (SEM), Scanning Transmission X-Ray Microscopes (STXM), and Scanning Transmission Electron Microscopes (STEM) as well as other instruments and analytical platforms.

In one set of tests one embodiment of the TEM liquid sample device with a window orientation described above was utilized. In some applications SiN chip membranes and a Si support frame of a generally square shape with typical dimensions of 3 mm by 3 mm were utilized. In another set of tests chip membranes and a Si support frame of a generally round shape with a typical diameter of 3 mm were utilized. Chip membranes included a thickness selected from about 10 nm to about 50 nm and a spacer thickness selected from about 100 nm to about 800 nm attached to the Si support frames with a typical thickness of about 100 μm resulting in a typical liquid sample layer thickness in the assembled device of from about 200 nm to about 1600 nm. In one set of tests chip membranes each included a single SiN window with rectangular shapes of various dimensions such as, for example, 50 μm by 200 μm and 30 μm by 200 μm oriented orthogonally to the opposing membrane window with a chip membrane thickness of 25 nm and a spacer thickness of 400 nm providing a liquid sample layer thickness in the assembled device of about 800 nm (2×400 nm) and a total device thickness of ~200 μm.

In other tests one or more vent apertures were introduced using SEM/FIB into one or more membrane windows on respective sides of the TEM liquid sample device 100 outside the transmission zone 14 to prevent sample bulging and to maintain chip membrane uniformity during TEM and multimodal imaging. In some tests vent apertures included sizes from about 700 nm to about 1000 nm but sizes are not intended to be limited. For example, in some applications vent apertures included sizes selected from about 500 nm to about 2 μm. In some applications vent apertures included a size less than or equal to about 1 μm to accommodate lower spatial resolution depths in the TEM as low as ~1 nm without needing to alter the liquid samples in the device such as by freezing or drying as performed in the prior art. Assembled TEM liquid sample devices of the present invention were then loaded into a standard type TEM solid sample holder or a standard type TEM sample heating holder such as Gatan® holders (Pleasanton, Calif., USA) and inserted into the TEM high vacuum for static and dynamic TEM sample imaging.

EXAMPLE 1

Figure 3B:
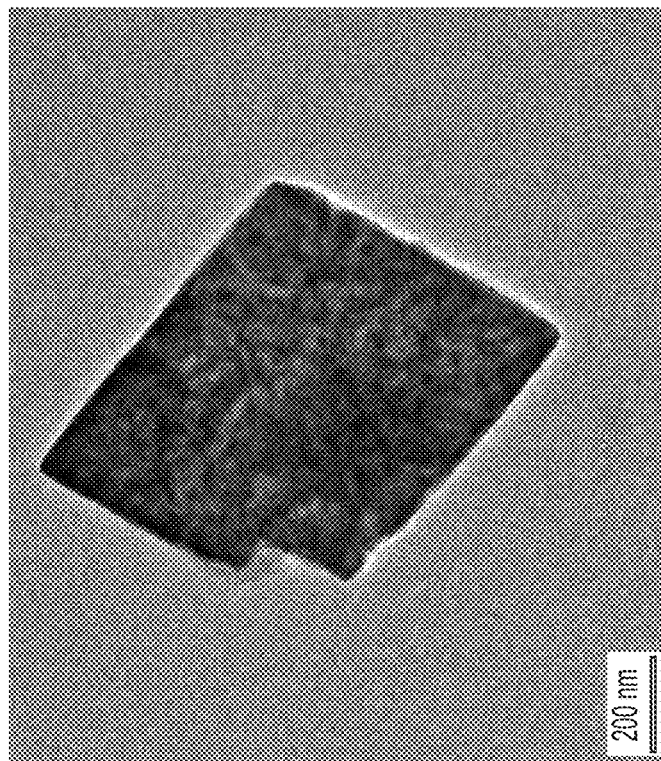
FIGS. 3A-3D show various TEM images and different multimodal images of liquid sample particles acquired in accordance with one embodiment of the present invention.
Figure 3A:
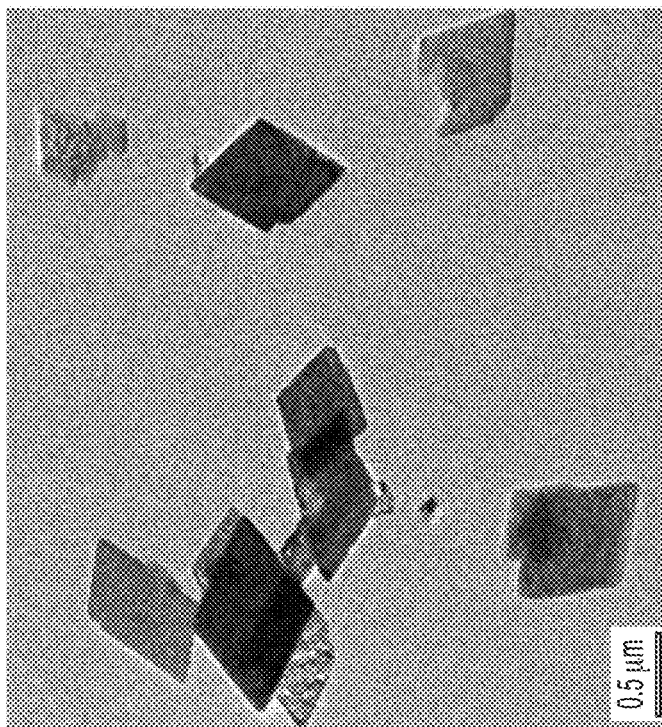

In one set of experiments one embodiment of the TEM liquid sample device was loaded with liquid samples containing AlOOH (e.g., APYRAL AOH-60 Boehmite, Nabaltec, Germany) particles in DI water at concentrations from about 10 micrograms per cubic meter (10 μg/m$^3$) to about 10 milligrams per cubic meter (10 mg/m$^3$) that were then loaded into a standard type TEM sample holder for TEM imaging of the particles in the liquid sample in situ in an Environmental TEM (ETEM) while under vacuum. Vacuum in the ETEM was sustained throughout the experiments from about 2×10$^{-7}$ mbar to about 1×10$^{-3}$ mbar. Vacuum inside the objective pole piece was maintained by differential pumping. The microscope was operated in the 80 kV to 300 kV range. Imaging analyses were performed utilizing standard TEM operation protocols. FIG. 3A shows a TEM image of a collection of AlOOH particles in the liquid sample obtained in high vacuum mode utilizing the present invention including a cluster of AlOOH particles and a few additional individual AlOOH particles. FIG. 3B shows a TEM image of a single AlOOH particle from the cluster of AlOOH particles in FIG. 3A.

Figure 3D:
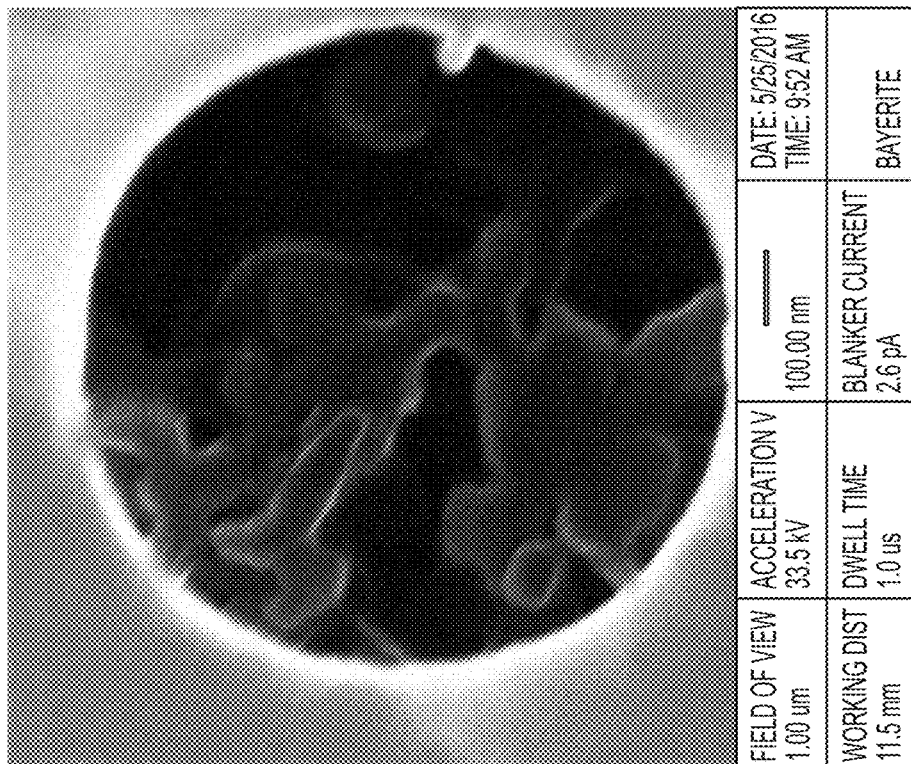
Figure 3C:
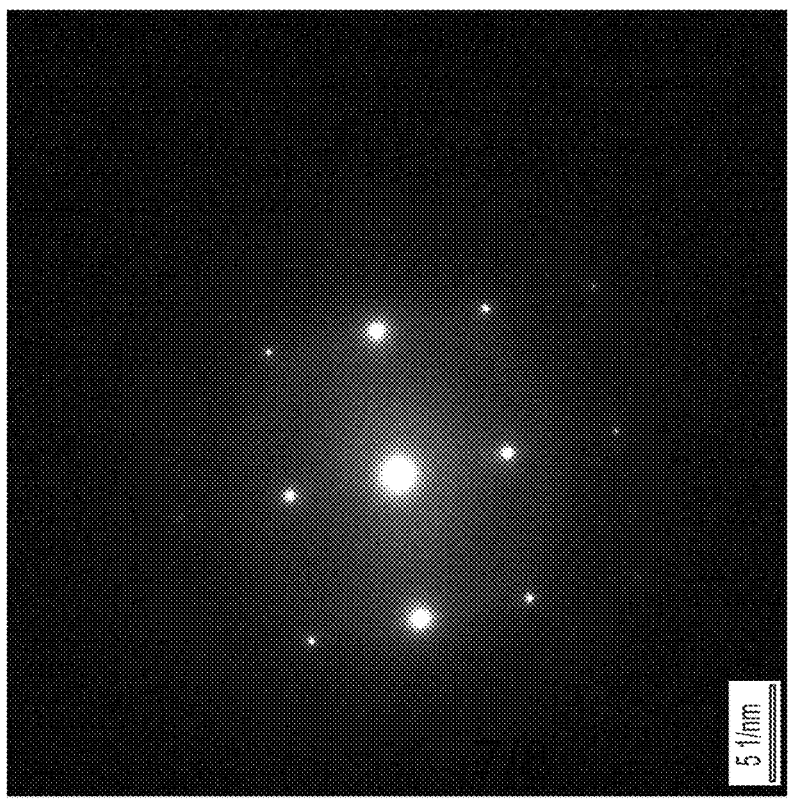

In another set of experiments multimodal capabilities of embodiments of the TEM liquid sample devices were tested. These devices containing the same liquid samples and materials previously imaged by TEM were then multimodally analyzed or imaged in other instrument platforms such as ED and HeIM. No changes to these devices or liquid samples were required prior to these multimodal analyses. FIG. 3C shows a multimodal electron diffraction pattern image of the same AlOOH particle viewed in FIG. 3B showing the crystal symmetry and lattice spacing of this particle. FIG. 3D shows another multimodal image of the same single AlOOH particle in FIG. 3B acquired with HeIM. Standard imaging conditions for each of these instrument platforms whether for TEM solid samples, ED solid samples, or HeIM solid samples were utilized demonstrating universality, utility, and advantages provided by the present invention for multimodal imaging of liquid sample materials in situ compared to prior art systems and approaches.

Figure 4A:
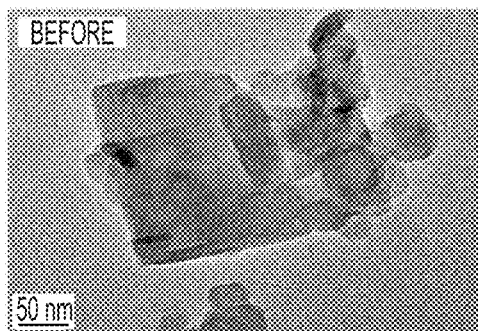
FIGS. 4A-4F show TEM images of liquid sample particles dynamically acquired as a function of time and temperature in accordance with one embodiment of the present invention.
Figure 4B:
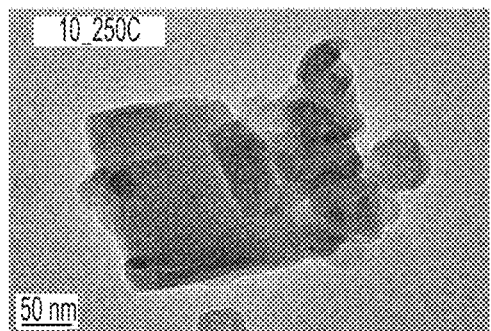
Figure 4C:
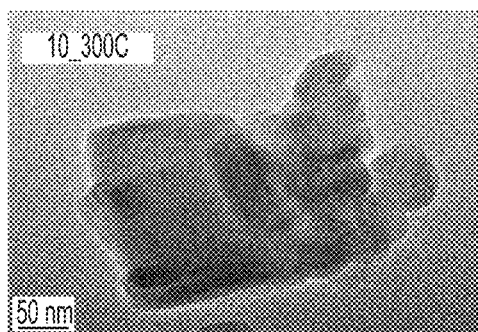
Figure 4D:
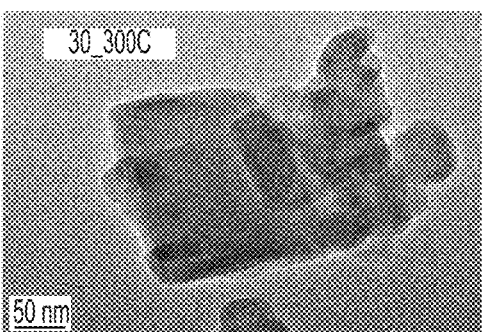
Figure 4E:
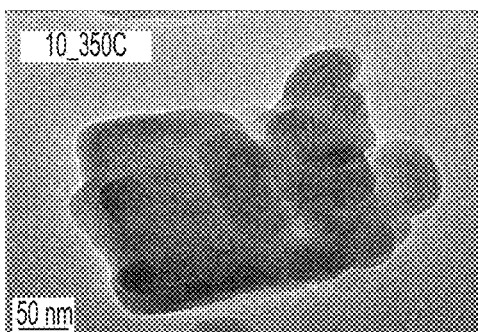
Figure 4F:
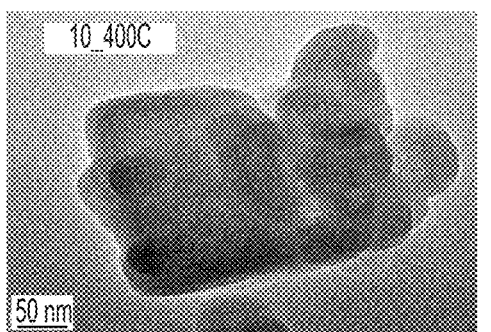

In another set of experiments different embodiments of the TEM liquid sample device were utilized to perform dynamic TEM imaging of liquid samples and materials. In one example liquid samples containing Bayerite [α-aluminum hydroxide or $Al(OH)_3$] particles (e.g., APYRAL AOH-180, Bayerite, Nabaltec, Germany) in DI water at a concentration of 100 micrograms per cubic meter (100 μg/m$^3$) were introduced between membranes of the SALVI-TEM device by pipette (total volume of ~20 μL) during assembly. The assembled device was then introduced into the TEM high vacuum in a standard type TEM solids heating holder. Vacuum (~10$^{-7}$ Torr) was maintained throughout these experiments allowing TEM images to be acquired dynamically under constantly changing conditions. Liquid samples were then heated under vacuum by ramping holder temperature from room temperature of about 21 degrees (° C.) to 400° C. in order to observe particle phase transformation in situ. Heating rates were selected from about 1° C. per min to about 20° C. per minute with a 4 hour run time on average. Liquid samples were first heated to 100° C. to remove water from inside the device cell and then held at 200° C. for 30 minutes to ensure water was removed as evidenced by pressure stabilization inside the cell. Cell was then heated, for example, to 400° C. at 50 degree increments and held at temperature for 30 min. TEM images of the same sample were dynamically acquired as a function of temperature and time to observe transformational particle changes as a result of dehydration and evolution of particle porosity both observations being indicative of particle phase transformation from displacement or exchange of atoms. Same samples were also multimodally analyzed by electron diffraction analysis. FIGS. 4A-4F show a series of high resolution TEM images of a same set of bayerite particles acquired dynamically in time-elapsed manner while dynamically heating these particles in a TEM solid sample heating holder under high vacuum conditions as a function of temperature and time from room temperature (4A) to 400° C. (4F) showing phase changes as the particles change from bayerite to $Al_2O_3$. FIG. 4A is an image of a cluster of bayerite particles in the liquid sample acquired at room temperature showing initial sharp particle shapes and edges. FIG. 4B is an image of the same bayerite particles after heating from room temperature to 100 degrees to remove water and then to 250 degrees which was held for 10 minutes at temperature. After water loss particle shapes and edges are not as sharp reflecting changes in particle structure. FIG. 4C is an image of the same bayerite particles after heating to 300 degrees and held 10 minutes at temperature. This image shows progressive changes to particle shape, morphology, and porosity at the particle surface with increasing pore size as a function of increasing temperature. FIGS. 4D-4E show subsequent images collected for these same sample particles at yet higher temperatures or longer times. Further progression in changes to particle shape, morphology, and porosity at the particle surface are evident. FIG. 4F is an image after heating the same sample particles to 400 degrees held 10 minutes at temperature. Large differences in particle shape, morphology, and porosity at the particle surface are evident compared to the same particles at room temperature (4A).

As these results demonstrate, embodiments of the present invention allow imaging of same liquid sample materials in situ in either static or dynamic conditions. TEM imaging data combined with other multimodal data collected in other instrument platforms from the same liquid sample materials utilizing embodiments of the present invention can be expected to find many varied applications in such areas as microanalysis using electron microscopy and focused spectroscopy; characterization of heterogeneous catalysts and catalytic processes; particle evolution and growth; particle morphology and structure; particle porosity; and predictive materials and processes.

The present invention provides novel and non-obvious advances in TEM liquid sample imaging as compared to prior art TEM liquid sample systems and approaches taught in the prior art. First, the invention utilizes standard type TEM chips compatible with standard type TEM sample holders thus eliminating need for specialized TEM chips and TEM liquid sample holders or specialized and involved sealing approaches utilized in the prior art. Second, vent apertures of the present invention address liquid sample bulging not resolved by systems and approaches taught in the prior art thereby providing a novel and non-obvious approach for enhanced TEM and multimodal image resolution, a significant advancement in the art. Third, invention devices have a significantly lower material and fabrication cost compared to prior art devices and are easily assembled. Fourth, device parameters are easily tailored or modified providing a high modular flexibility and versatility enabling multimodal imaging and analyses of the same liquid sample materials in other analytical platforms such as a HeIM. Fifth, the invention enables dynamic TEM imaging of liquid sample materials in situ not previously achieved with prior art systems and approaches.

While preferred embodiments of the present invention have been shown and described, it will be apparent to those of ordinary skill in the art that many changes and modifications may be made without departing from the invention in its true scope and broader aspects. Appended claims are therefore intended to cover all such changes and modifications as fall within the spirit and scope of the present invention.

What is claimed is:

1. A liquid sample device for imaging and analyses using a probe beam, comprising:
    a sample chamber defined by a pair of membranes forming a sample inlet and outlet, each membrane defining a non-opaque window and at least one membrane defining a vent aperture, said chamber configured to hold a preselected quantity of a liquid sample therein while a probe beam passes through said window and internal gases are vented through said vent aperture.

2. The device of claim 1 further comprising a frame sandwiched between the two membranes so as to impart a preselected height to said sample chamber.

3. The device of claim 1 further comprising a spacer positioned between said membranes so as to provide a preselected optical characteristic to an image created by said probe beam.

4. The device of claim 1 further including a sample injection port configured to allow delivery of the liquid sample to the sample chamber.

5. The device of claim 1 wherein the liquid sample introduced into the sample chamber occupies the entire height of the sample chamber.

6. The device of claim 1 wherein the windows in each membrane are aligned to define a probe beam transmission zone.

7. The device of claim 6 wherein the vent aperture is disposed external to the probe beam transmission zone.

8. The device of claim 1 wherein the assembled device is configured for insertion into a standard type TEM sample holder without modification of the TEM sample holder.

9. The device of claim 1 wherein the vent aperture is dimensioned to retain the liquid sample within the sample chamber when the TEM vacuum is applied.

10. The device of claim 1 wherein the first membrane contains a different number of windows than the second membrane.

11. A liquid sample chip for dynamic TEM imaging and multi-modal analyses of liquid samples and materials therein in situ, the chip comprising:
   a sample chamber defined by a pair of membranes defining a sample inlet and outlet, each membrane defining a non-opaque window and a vent aperture, said chamber configured to hold a preselected quantity of a liquid sample at a generally uniform thickness therein while a probe beam passes through said window and internal gases are vented through said vent aperture;
   a frame sandwiched between the two membranes so as to impart a preselected height to said chamber; and
   a spacer positioned between said pair of membranes so as to provide a preselected optical characteristic to an image created by said probe beam.

12. The device of claim 11 wherein the assembled device is configured for insertion into a standard type TEM sample holder without modification of the standard TEM sample holder.

13. The device of claim 11 wherein the first membrane contains a different number of windows than the second membrane.

14. A method for TEM imaging of liquid samples comprising the step of:
   performing TEM imaging of a liquid sample in a sample chamber defined by a pair of membranes defining a sample inlet and outlet, each membrane defining a non-opaque window and at least one membrane defining a vent aperture said chamber configured to hold a preselected quantity of a liquid sample therein at a generally uniform thickness while a probe beam passes through said window and internal gases are vented through said vent aperture.

15. The method of claim 14 further including the step of injecting the liquid sample through an injection port to deliver the liquid sample to the sample chamber.

16. The method of claim 14 further including the step of imaging or analyzing the same liquid sample using another analytical platform.

17. The method of claim 14 wherein the first membrane contains a different number of windows than the second membrane.

* * * * *

UNITED STATES PATENT AND TRADEMARK OFFICE
CERTIFICATE OF CORRECTION

| | | |
|---|---|---|
| PATENT NO. | : 10,598,609 B2 | Page 1 of 2 |
| APPLICATION NO. | : 15/483939 | |
| DATED | : March 24, 2020 | |
| INVENTOR(S) | : Xiao-Ying Yu, Libor Kovarik and Bruce W. Arey | |

It is certified that error appears in the above-identified patent and that said Letters Patent is hereby corrected as shown below:

On the Title Page

Item (56) References Cited, page 2, 1st Column, 27th Line - Replace "7,387,715 B2 8/2008 Vogel et al." with --7,387,715 B2 6/2008 Vogel et al.--

Item (56) References Cited, page 2, 1st Column, 32nd Line - Replace "9,022,662 B2 5/2015 Chupas et al." with --9,022,652 B2 5/2015 Chupas et al.--

Item (56) References Cited FOREIGN PATENT DOCUMENTS, page 2, 1st Column, 65th and 66th Line - Remove - "WO PCT/US2018/026708 10/2019"

Item (56) References Cited OTHER PUBLICATIONS, page 3, 2nd Column, 50th Line - Add --WO PCT/US2018/026708 IPRP dated Oct. 15, 2019, Battelle Memorial Institute--

Item (56) References Cited, page 3, 2nd Column, 1st Line - Replace "Dowsett, M. G., et al., Cell for Simultaneous Synchotron Radiation" with --Dowsett, M. G., et al., Cell for Simultaneous Synchrotron Radiation--

Item (56) References Cited, page 3, 2nd Column, 7th Line - Replace "active active surface area of polycrystalline gold electrode, Elec" with -- active surface area of polycrystalline gold electrode, Elec---

Item (56) References Cited, page 3, 2nd Column, 17th Line - Replace "Lithium Batteries Using Synchotron Radiation, Journal of the" with --Lithium Batteries Using Synchrotron Radiation, Journal of the--

Item (56) References Cited, page 3, 2nd Column, 24th Line - Replace "Instuments, 75, 5, 2004, 1251-1254." with --Instruments, 75, 5, 2004, 1251-1254.--

Signed and Sealed this
Fourteenth Day of December, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,598,609 B2

Item (56) References Cited, page 3, 2nd Column, 32nd Line - Replace "envoronments in surface electrochemistry, Surface Science, 335," with --environments in surface electrochemistry, Surface Science, 335,--

Item (56) References Cited, page 3, 2nd Column, 36th Line - Replace "WO PCT/US2018/026708 Search Rept., dated Oct. 15, 2016, Bat" with --WO PCT/US2018/026708 Search Rept., dated Oct. 15, 2018, Bat- --